United States Patent [19]

Ashkinazy

[11] Patent Number: 4,522,596

[45] Date of Patent: Jun. 11, 1985

[54] MODULAR IMPLANT ASSEMBLY

[76] Inventor: Larry R. Ashkinazy, 200 Central Park South, New York, N.Y. 10019

[21] Appl. No.: 572,435

[22] Filed: Jan. 20, 1984

[51] Int. Cl.³ .............................................. A61C 8/00
[52] U.S. Cl. .................................... 433/173; 433/176
[58] Field of Search ................ 433/173, 174, 175, 176

[56] References Cited

U.S. PATENT DOCUMENTS

| | | | |
|---|---|---|---|
| 3,919,772 | 11/1975 | Lenczycki | 433/173 |
| 3,981,079 | 9/1976 | Lenczycki | 433/174 |
| 4,177,562 | 12/1979 | Miller et al. | 433/174 |
| 4,225,668 | 9/1980 | Bartoli | 433/176 |
| 4,379,694 | 4/1983 | Riess | 433/173 |
| 4,420,305 | 12/1983 | Linkow | 433/176 |

FOREIGN PATENT DOCUMENTS

| | | | |
|---|---|---|---|
| 882466 | 7/1953 | Fed. Rep. of Germany | 433/174 |
| 770696 | 3/1957 | United Kingdom | 433/174 |

*Primary Examiner*—John J. Wilson
*Attorney, Agent, or Firm*—Natter & Natter

[57] ABSTRACT

A modular implant assembly utilizes standardized components removeably attachable to a base module. The module is anchored to the bone tissue and provided with a matrix of apertures and a series of sockets for threadably receiving the interchangeable components including a support post for an artificial tooth structure, a threaded pin for stabilizing the module within the bone tissue and other stock parts. The apertures and sockets are randomly accessable by the components which are externally insertable through the bone tissue. The components are further divisible into constituent elements and can be constructed in various combinations for attachment to the module. In a variant embodiment the module defines a cylindrical surface. A transverse cross bar extending diametrically over the cylindrical opening includes an aperture for accepting a vertical support post. In addition, the apertures within the cylindrical side surface will accommodate an anchor pin for preventing dislodgement. In another form the module is secured in overlying relationship with respect to the bone tissue and affixed by the threaded pins. A support post is insertable within a selected aperture for positioning an artificial tooth structure.

22 Claims, 10 Drawing Figures

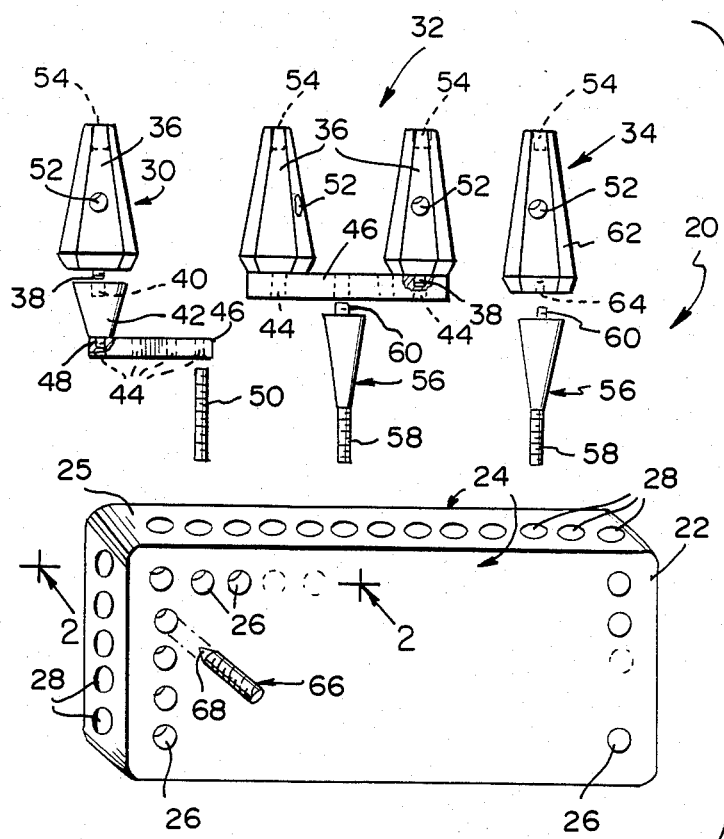
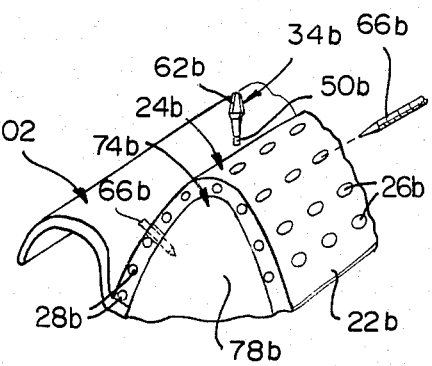
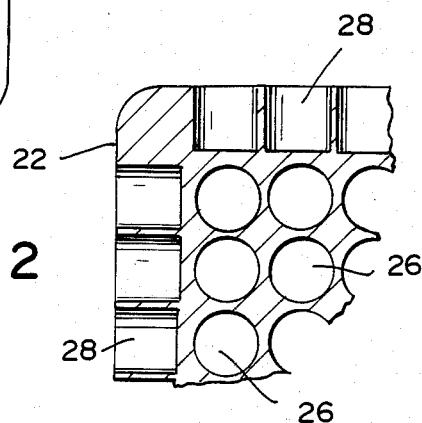
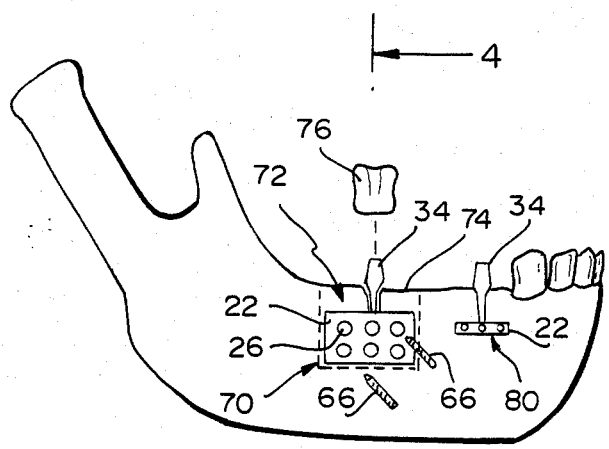
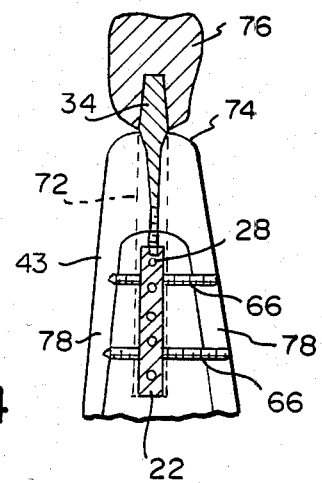
FIG. 1
FIG. 10
FIG. 2
FIG. 3
FIG. 4

MODULAR IMPLANT ASSEMBLY

TECHNICAL FIELD

This invention concerns medical implants and especially a modular implant assembly for dental prosthesis.

In particular, the implant assembly of this invention relates to an ersatz root having modular attachments which can be combined in different arrangements.

BACKGROUND ART

The development of dental techniques for replacing missing teeth included the installation of either permanent endosteal or subperiosteal anchor devices. Those implant devices were used for supporting an artificial tooth, crown, or a dental bridge.

Prior implant technology, incorporating endosteal root replacement, utilized a substantially planar member, such as a blade, loop, furcated stem, or similar element which was inserted within a prepared channel generally lying in a vertical plane with respect to the alveolar ridge. The planar member, when seated within this crypt, had an integral post projection above the bone on the ridge crest for accepting a dental prosthesis. That procedure was generally illustrated in U.S. Pat. Nos. 3,465,441 and 4,044,467.

A problem encountered with vertical placement was that precision cutting of the channel was required in order to assure sufficient confinement within the bone structure to prevent dislodgment. Another inherent shortcoming of the vertically oriented implant was that if an adequate amount of bone height or width was not present, such as proximate the shallow clearance under the maxillary sinus, the regions of the tuberosity, the mandibular nerve, or at similar anatomical landmarks, customized shapes or sizes were required; however, even those "special" implants presented accommodation problems. A further limitation was that the design of those vertical placed implants frequently included a sharp cutting edge and an impact force was required, such as through the application of a surgical mallet, for seating the implant into the osseous tissue. This often resulted in trauma to the bone. A further deficiency was that the anchorage was dependent upon frictional fit and not upon positive stabilization.

Previous attempts to avoid some of the above-referenced problems of the vertically positionable implants included use of horizontally oriented blade implants such as shown in U.S. Pat. No. 3,925,892. That implant device included a plate and post structure which necessitated surgically providing a horizontal groove as well as a vertical slot for reception of the post. A disadvantage of that procedure was that an additional surgical step was required for providing the vertical slot and, furthermore, difficulties were presented in locating the vertical slot such that the post and crown would be in alignment with the remaining teeth. Another deficiency of that procedure was that the vertical slot removed bone structure critically needed for resisting lateral forces as applied to the post during occlusal loading.

Still another method for securing a horizontal planar implant was shown in U.S. Pat. No. 3,919,772. That procedure, however, was limited to horizontal implants only and required the use of a dental jig for accurately drilling vertical bores in the jawbone such that a post could be inserted and properly aligned for mating with the horizontal blade.

Another problem in dental prosthesis, as previously encountered, was to provide reliable anchoring for long-term retention of the implant and for withstanding occlusive forces. The use of stabilizer bars, for example, had been applied to vertically oriented blade implants such as shown in U.S. Pat. No. 4,044,466. In order to locate the stabilizer bars, however, a positioning guide was required and, furthermore, this method was limited to vertical blade implants.

A still further anchoring arrangement applied a camming action as was illustrated in U.S. Pat. No. 4,177,562. That system also had its shortcomings in that its application was recommended for vertical insertion. The expandable retention was also dependent upon buccal-lingual dimension of the bone and the application of appropriate pressure so as not to traumatize or fracture the surrounding bone.

It should also be noted that the aforementioned implant devices were adapted for endosteal or within the bone embedment only whereas the instant invention further encompasses subperiosteal applications, i.e. placement on top of the bone tissue.

Although some devices have been previously employed for subperiosteal implantation, such as illustrated in British Pat. No. 770,696, the perforated mesh shown therein was not provided with apertures along its edges as in this invention. Further, the aforementioned implant devices did not encompass a modular assembly having separable components adapted for alternate interfitting arrangements.

DISCLOSURE OF THE INVENTION

To briefly summarize, the nature of this invention concerns a modular implant assembly which utilizes a combination of components that can be selectively interconnected to a base module. The purpose of this implant assembly is to provide a universally adaptable dental implantology system which can be readily connected in flexible arrangements suitable for both endosteal and subperiosteal accommodation at selected maxillary and mandibular sites.

The structure of the instant invention includes a base module forming a foundation for distribution of occlusive forces. The module is provided with a plurality of openings for attaching standardized components. These components include a post for supporting an artificial tooth, a pin for stabilizing the module to the bone, a bar for providing intermediate support, a bolt for interconnecting modules, and other stock members. In addition, the several components such as the posts, can be further brokendown into constituent parts. These components and the constituent parts can be erected in various combinations and attached to the module in multiple selected arrangements. The standardization of these units and their interchangeable use capabilities greatly reduce inventory requirements. It should also be noted that the openings within the module which are not occupied by the components are subject to interlocking tissue growth which improves the retention characteristics of the module assembly.

In accordance with this invention, the module is fabricated from a material which can be suitably severed, shaped and united with the bone structure. It should be apparent that the module can thus be tailored by trimming to desired dimensions and forming to required shapes and configurations for accommodation at various bony region sites while avoiding anatomical obstructions. This technique of customizing the module to existing conditions can be achieved with substantially no waste material because the severed module pieces can be combined with other modules or scrap segments or otherwise incorporated within new implant assemblies. It should also be apparent that the component elements can be individualized through the selective interconnection of their constituent parts.

Another feature attributable to this implant assembly is the facility for repairing damage or failure to an installed implant assembly. Since the components are removable from the base module, replacements can be made while utilizing a previously implanted module. It should also be noted that portions of the implanted module can be accessed by excavation and then cut and removed in situ with substitute sections attached to the module or appropriate repairs made to the module.

The versatility of applications of the implant assembly is further enhanced because the openings for accepting the components are uniformly spaced apertures in a side face forming a dispersion pattern or matrix of receptor stations for "blind spotting" and random registration by the components which can be exteriorly inserted through the bone structure for engagement with the module. This capability minimizes the sequential surgical procedures for implantation. In addition, recesses in the form of sockets are provided along a peripheral margin of the module for receiving the standardized components and thus expanding the multifunctional aspects of this implant device.

In view of the foregoing, it should be apparent that the present invention overcomes many of the problems, disadvantages and shortcomings of the prior art and provides a modular implant assembly which avoids many of the drawbacks previously encountered.

Having thus summarized the invention, it will be seen that it is an object thereof to provide a modular implant assembly of the general character described herein which is not subject to the aforementioned limitations.

Specifically, it is an object of this invention to provide an implant assembly having a base module and complimentary components which can be combined in discretionary arrangements with the base module as indicated by prosthesis requirements and anatomical conditions.

Another object of this invention is to provide an implant assembly including a module having receptor stations for engagement by externally insertable standardized components.

Still another object of this invention is to provide an implant assembly having components which can be divisible into constituent parts and adapted for individualized combinations.

Yet another object of this invention is to provide an implant assembly adapted for dental prosthesis which provides greater flexibility of application, increased stability and improved reliability.

Other objects, features and advantages of the invention will in part be obvious and will in part be pointed out hereinafter.

With these ends in view, the invention finds embodiment in certain combinations of elements and arrangements of parts by which the object aforementioned and certain other objects hereinafter attained, all as more fully described with reference to the accompanying drawings and the scope of which is more particularly pointed out and indicated in the appended claims.

BRIEF DESCRIPTION OF THE DRAWINGS

In the accompanying drawings in which is shown possible exemplary embodiments of the invention:

FIG. 1 is a perspective view showing a planar base module having a grid pattern of transverse apertures and a plurality of marginal sockets extending normally to the peripheral edge and also showing several modular components;

FIG. 2 is a partial sectional view to an enlarged scale taken substantially along line 2—2 of FIG. 1 illustrating the marginal sockets and the transverse apertures;

FIG. 3 is a pictorial representation demonstrating two endosteal implant locations; one having a substantially horizontally placed module and the other site showing an alternate vertically embedded module;

FIG. 4 is a sectional view to an enlarged scale taken substantially along line 4—4 of FIG. 3 with a pair of anchor pins in engagement with the module;

FIG. 10 is a perspective view showing a subperiosteal implant installation.

BEST MODE FOR CARRYING OUT THE INVENTION

Figure 5:
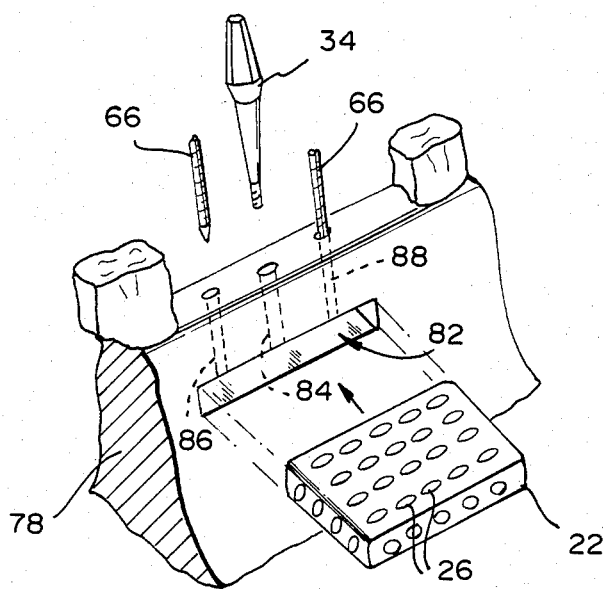
FIG. 5 is a partial perspective view illustrating installation of a horizontal module and mating components.

Referring now in detail to the drawings, the reference numeral 20 denotes generally a modular implant assembly in accordance with this invention. For the purpose of this exemplary embodiment, the invention will be discussed with regard to dental applications although the implant may be adapted for orthopedic, veterinary and other medical uses.

The implant assembly 20, as typically shown in FIG. 1, includes a base module 22. The module 22, for the purpose of this description, is shown as being a substantially planar member having a pair of parallel side faces 24 and an edge surface 25. A plurality of apertures 26 extend transversely through the side faces 24 and are preferably dispersed in a uniform grid pattern. In addition, a series of sockets 28 are distributed along and extend normal to the edge surface 25. The apertures 26 and the sockets 28 provide receptor stations for accommodating various components as will be hereinafter described.

The module 22 can be fabricated of titanium, vitalium, a ceramic composition or other bio-compatible materials. The side faces 24 as well as the edge surface 25 can be prepared with a roughened texture for increasing surface contact between the module 22 and the surrounding bone tissue. The apertures 26 and the sockets 28 are internally threaded and will similarly provide increased surface for improving bone retention properties.

In connection with this illustration, the dimensions of a typical module 22 can range from 5 mm. to 30 mm. in length, 2 mm. to 10 mm. in height with a thickness dimension of approximately 1.5 mm. The apertures 26 and sockets 28 have an inside diameter of approximately 1 mm. and are internally threaded. The sockets 28 extend to a depth of 1.5 mm. to 5 mm.

Further in regard to the components securable to the module 22, there is shown in FIG. 1 three exemplary support posts 30, 32, 34. The posts 30, 32, 34 are each comprised of a sub-assembly of separable elements that can be interchangeably connected to form units of varying complexity and function. By way of example, the support post 30 has a head element 36 and a threaded stud 38 for engagement within a socket 40 formed in a pedestal element 42 A series of apertures 44 are formed in a cross bar element 46. These apertures 42 accommodate a stud 48 extending from the pedestal 42 and a threaded shank 50. In addition, the head 36 includes an auxiliary aperture 52 and an auxiliary socket 54. The head 36 can thus be used to support a dental prosthesis device or alternately the aperture 52 and socket 54 can be used for accommodating additional components. It should further be pointed out that the studs 38, 48 and shank 50 are compatible with the apertures 26 and sockets 28 and can be connected directly to the module 22. Similarly, the shank 50 can be inserted within the socket 40, 54 and the aperture 52. Furthermore, an additional head 36 can be placed in tandem by securing the stud 38 within the socket 54 of another head 36.

The post 30 provides a right angle offset configuration which finds typical application wherein an implant site for the module 22 is not readily alignable with existing tooth structure. Other constructions include the support post 32 which provides a capacity for supporting two artificial tooth structures and support post 34 which shows a basic support arrangement.

The support post 32 utilizes the same head 36 and cross bar 46 and also has a modified pedestal element 56 which incorporates an integral threaded shank portion 58 and a threaded stud 60. The support post 34 employs the pedestal 56 with an alternate head element 62. The head 62 is similar to the head 36 with the exception that it has a socket 64 for receiving the stud 60.

Another component adapted for attachment to the module 22 is an anchor pin 66. The pin 66 has an externally threaded surface and a pointed nose 68 and is intended for complimentary threaded fit within a selected aperture 26 or socket 28. The threaded components, such as pin 66, can also be of a self-tapping design or can employ a frictional fit or adhesive bond. The nose 68 is adaptable for penetrating bone tissue to stabilize the module 22 and prevent dislodgement. It should also be clear that one or more of the support posts, 30, 32, 34 can be used with a single module 22 when either in a vertical or horizontal orientation.

The use of the implant assembly 20 will be discussed in regard to specific applications as illustrated in FIG. 3-5 showing two alternate endosteal installations.

A first implant site 70 shows the module 22 submerged within a vertical channel 72 formed within a ridge crest 74. The support post 34 has been threadably engaged within a selected one of the sockets 28 and is adapted for receiving an artificial tooth structure 76 or, for example, an end of the cross bar 46 can be engaged within the aperture 52 for constructing a dental bridge. It should also be noted that the module 22 can be trimmed to conform to the space limitations and the scrap portions of the module 22 can be combined with other segments or otherwise used independently.

Furthermore, in accordance with the technique of this invention, the module 22 is stabilized or anchored to the surrounding bone tissue 78 by use of the anchor pins 66. The pins 66 are inserted from an external position and will pass through bone tissue 78 to randomly access an aperture 26. The frequency and placement of the apertures 26 permit this random access registration without utilization of drill templates or other guidance apparatus. In addition, the anchor pin 66 can be inserted through drilled openings in the bone tissue 78; the excess length can then be removed.

The installation of the module 22 at a secondary location 80 shows a horizontal placement as may be required with shallow bone depth or for other anatomical reasons. As best shown in FIG. 5, a horizontal channel 82 is provided within the bone structure 78 and a vertical bore 84 is then located at a desired point and extended downwardly to intercept with the horizontal channel 82. The module 22 can then be inserted within the horizontal channel 82 and the support post 34 passed through the bore 84 and threadably connected to a randomly accessed aperture 26. The anchor pins 66 can also be inserted vertically within drilled holes 86, 88 for engagement with respective apertures 26. It should be noted that, in accordance with the method of this invention, a vertical slot is not required for positioning the post 34 and, therefore, bone structure 78 will surround the post 34 to provide lateral support.

Figure 7:
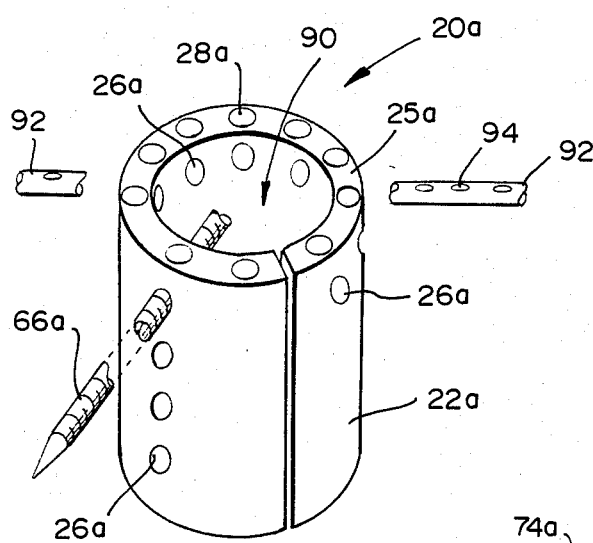
FIG. 7 is a variant embodiment showing a module in a cylindrical conformation including an obliquely insertable anchor pin and a cross bar.
Figure 9:
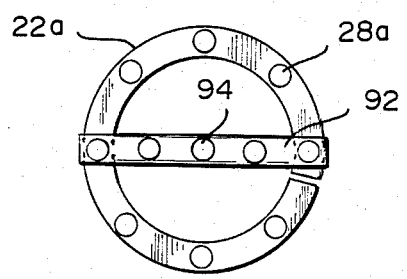
FIG. 9 is a plan view of the module of FIG. 8 showing the cross bar lying diametrically over the cylincrical opening.
Figure 8:
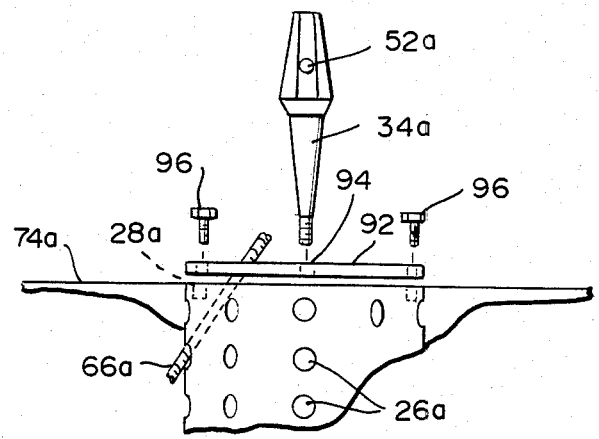
FIG. 8 is a partial sectional view in exploded fashion of the module of FIG. 7 implanted within a ridge crest showing attachment of the cross bar and a prosthesis post.

Another adaptation of the implant assembly 20 of this invention is illustrated in FIGS. 7-9 wherein like numerals have been used to represent corresponding parts with the suffix "a" added This alternate embodiment illustrates a cylindrical configuration wherein a base module 22a is insertable within a circular bore implant site. The module 22a can be formed by bending the substantially planar module 22. The module 22a includes a plurality of apertures 26a and sockets 28a. An anchor pin 66a can be inserted through an open end 90 of the module 22a and through an aperture 26a for penetration of the surrounding bone tissue 78a. A support post 34a can be secured to the circular module 22a by threadable engagement within a socket 28a. Another form for securement utilizes a cross bar 92 (substantially identical to cross bar 46) containing a plurality of apertures 94. The cross bar 92 is placed diametrically over the open end 90 and fastened to an edge surface of the module 22a by threaded bolts 96 passing through respective apertures 94 and secured within sockets 28a. The post 34a can then be connected with a selected aperture 94 within the cross bar 92. It should thus be apparent that there are available many alternate assembly arrangements using the basic components.

Figure 6:
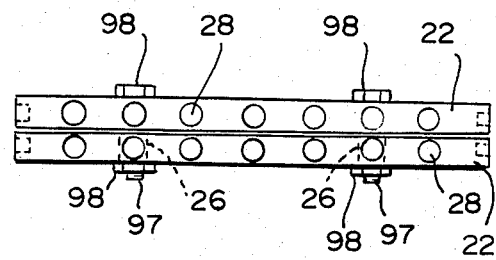
FIG. 6 is a plan view to an enlarged scale typically illustrating an arrangement combining two confronting modules locked in parallel juxtaposition.

In FIG. 6 there is shown a combination of two modules 22 which have been joined in juxtaposition by a pair of connecting pins 97 which are threaded for complimentary fit through respective apertures 26 and further adapted for accepting suitable nut fasteners 98 at their opposite ends. This demonstrates the versatility afforded and can, for example, be used in situations wherein the width dimensions of a pre-existing implant channel exceeds the thickness of a single module 22.

In a similar manner, the overall width dimension of the two modules 22 can be varied such as by adjusting the spacing between the confronting modules.

A further application of the implant assembly shown in FIG. 10 is addressed to a subperiosteal installation.

This application is intended for use in those situations wherein an insufficient amount of bone structure is available for either vertical or horizontal embedment and further illustrates the flexibility of the invention. The suffix "b" has been used for identifying like corresponding parts.

A module 22b, in this embodiment, is shaped to conform to the ridge crest 74b and is affixed to the bone tissue 78b by using the anchor pins 66b. The gum 102 is shown as cut open to expose the bone tissue 78b. A modified support post 34b is insertable within a selected aperture 26b overlying the ridge crest 74b. The support post 34b is substantially similar to support post 34 however, being of a shorter height dimension which can be achieved by substituting a threaded shank 50b in place of the pedestal 56 and attaching a head 62b to the shank 50b. Thus, it will be seen that there is provided an implant assembly which achieves the various objects of the invention and which is well adapted to meet conditions of practical use.

Since other possible embodiments might be made of the present invention or changes incorporated in the exemplary embodiment set forth, it is to be understood that all materials shown and described in the accompanying drawings are to be interpreted as illustrative and not in a limiting sense.

Having thus described the invention, there is claimed as new and desired to be secured by Letters Patent:

1. An implant assembly using a combination of modular components comprising a base module adapted for endosteal and subperiosteal implantation to a bone structure at selected sites, said module having a pair of opposed side faces defining a matrix of apertures extending transversely through the module and peripheral edge surfaces including a plurality of sockets extending normally along at least one of said edge surfaces, said apertures and said sockets having attachments means for engaging a component means, said component means being randomly registrable with either of said apertures or sockets and adapted to stabilize the module with respect to the bone structure and to support a prosthesis.

2. An implant assembly as claimed in claim 1 wherein the component means are adapted for removable securement to the module.

3. An implant assembly as claimed in claim 2 wherein the component means includes a sub-assembly of separable elements, said elements being interchangeable connectable in alternate combinations and securable to the module.

4. An implant assembly as claimed in claim 2 wherein the component means are further adapted for connecting a plurality of modules.

5. An implant assembly as claimed in claim 4 wherein the component means includes a pin adapted for interconnecting a plurality of modules and the attachment means includes a nut fastener.

6. An implant assembly as claimed in claim 1 wherein the component means includes a first component registrable with either of said apertures or sockets for stabilizing the module with respect to the bone structure and a second component being concurrently engageable with another of said apertures or sockets for supporting a prosthesis.

7. An implant assembly as claimed in claim 6 wherein the first component comprises an anchor pin.

8. An implant assembly as claimed in claim 7 wherein the second component comprises a post, said post being adapted for supporting a dental prosthesis.

9. An implant assembly as claimed in claim 8 wherein the post includes a head for receiving the dental prosthesis, a pedestal securable to said head and a shank, said shank being engageable with the attachment means of said apertures and sockets.

10. An implant assembly as claimed in claim 9 wherein said head includes at least one opening, said opening including attachment means for engaging said components.

11. An implant assembly as claimed in claim 10 wherein the head is laterally positionable with respect to the shank for selective alignment of a dental prosthesis with existing tooth structure.

12. An implant assembly as claimed in claim 1 wherein the module is severable to facilitate accommodation within an implant site.

13. An implant assembly as claimed in claim 1 wherein the module is cylindrically shaped.

14. An implant assembly as claimed in claim 13 further including a cross-member, said cross-member being securable to the edge surface of the module.

15. An implant assembly as claimed in claim 14 wherein said cross-member defines openings, said openings including attachment means for engaging said components.

16. An implant assembly as claimed in claim 1 wherein the attachment means comprises an internally threaded surface within the apertures and the sockets and a complementary externally threaded surface on the component means.

17. An implant assembly as claimed in claim 1 wherein the sockets extend normal to each of the edge surfaces.

18. An implantology technique using modular components including a base module adapted for horizontal or vertical implantation, said module having a plurality of transverse apertures and having a series of sockets extending normally to the apertures, said apertures and sockets including fastening means for engaging said components, the method comprising the steps of:
  positioning the base module at a prepared implant site for securement to a bone structure, and
  randomly registering a component within an aperture or socket for engagement with the fastening means.

19. An implantology technique as claimed in claim 18 including the step of:
  attaching another component to either of an aperture or socket by engagement with the fastening means.

20. An implantology technique as claimed in claim 19 including as an initial step:
  placing the base module in overlying relationship with respect to the bone structure.

21. An implantology technique as claimed in claim 20 including the step of:
  severing the base module to conform with space requirements wherein the severed waste portion can be reclaimed for further usage.

22. An implantology technique as claimed in claim 19 including the step of:
  interconnecting a plurality of modules by engagement with the components.

* * * * *